United States Patent [19]
Morgan et al.

[11] Patent Number: 5,371,585
[45] Date of Patent: Dec. 6, 1994

[54] PARTICLE DETECTING INSTRUMENT WITH SAPPHIRE DETECTING CELL DEFINING A RECTANGULAR FLOW PATH

[75] Inventors: Gary L. Morgan, Elkridge; Charles F. Harrison, Adelphi, both of Md.

[73] Assignee: Pacific Scientific Company, Newport Beach, Calif.

[21] Appl. No.: 973,383

[22] Filed: Nov. 10, 1992

[51] Int. Cl.$^5$ ............................................. G01N 21/05
[52] U.S. Cl. ..................................... 356/246; 356/339
[58] Field of Search ......................... 356/246, 440, 339

[56] References Cited

U.S. PATENT DOCUMENTS

| | | | |
|---|---|---|---|
| 3,972,627 | 8/1976 | Rabl et al. | 356/246 |
| 4,076,420 | 2/1978 | De Maeyer et al. | 356/246 |
| 4,802,768 | 2/1989 | Gifford et al. | 356/365 |
| 4,818,103 | 4/1989 | Thomas et al. | 356/72 |
| 5,125,737 | 6/1992 | Rodriguez et al. | 365/39 |

FOREIGN PATENT DOCUMENTS 1498775 1/1969 Germany ............................ 356/246

Primary Examiner—Richard A. Rosenberger
Attorney, Agent, or Firm—Lane, Aitken & McCann

[57] ABSTRACT

In a particle detecting instrument, a sapphire detecting cell is provided with a square flow path. The sapphire cell is assembled from four sapphire pieces which extend throughout the length of the cell. The cell has a central section containing the square flow path with planar exterior walls and cylindrical end sections. The pieces are separated by black gaskets which are sandwiched between the opposed faces of the pieces. The pieces are clamped together by shape memory alloy rings which engage the cell in the cylindrical end sections. Each sapphire piece has a polished planar interior surface defining one of the walls of the square flow path.

24 Claims, 3 Drawing Sheets ered to flow. The flow cell is provided with transparent walls so that a light beam can be transmitted through the flowing fluid. Particles passing through the light beam scatter light to a photodetector which generates pulses in response to the scattered light. The characteristics of the pulses, such as the pulse amplitudes, provide a measurement of the particle sizes. The detected scattered light may be forward scattered in the direction of the light beam or scattered at right angles to the light beam. Right-angle scattering geometry is preferred because it minimizes interference from stray light scattered from the entrance and exit windows of the cell. Right-angle scattering geometry requires the cell walls be transparent to the light all around the flow path. Early detecting cell designs with transparent walls surrounding the flow path utilize a polished round flow path. When a laser beam is focused to a narrow dimension illuminating the center of the flow path and suitable polish is present both on the outside and inside walls of the cell, the background scattered light from the cell will be sufficiently low to permit detection of scatter from particles as small as 0.1 microns in diameter. Round flow paths, however, have a drawback in that the laser beam cannot be broadened to illuminate a large area of the cell without increasing the background light to unacceptable levels. Accordingly, the view volume of such a cell is limited generally to less than 1 percent of the cell.

To overcome this problem, there has been developed a cell with a highly polished square flow path. This is accomplished with cells having quartz walls by making the cell out of four flat pieces which are highly polished and then diffusion bonding the polished pieces together. With this geometry, the laser beam can be widened to illuminate a much larger percentage of the flow path while still maintaining a low level of background scatter. With a quartz detection cell having a square flow path, the beam can be widened to cover 90 percent of the view volume and particles having a diameter of 0.2 microns can be detected. Particles having a diameter of 0.1 micron can be detected with a view volume of 4 percent of the flow path. Thus, the use of diffusion bonded quartz walls defining a rectangular flow path provides a highly efficient detecting cell.

However, quartz cannot be used to make up the walls of the detection cell if the fluid is corrosive and liquids containing particles to be measured are frequently too corrosive to pass through a quartz detection cell. When the fluid is corrosive, sapphire is the material of choice for the detection cell walls because it is not susceptible to being corroded by corrosive liquids. However, sapphire cannot be effectively diffusion bonded and, accordingly, the technique of providing a rectangular flow path as described above for the quartz cell cannot be used with sapphire.

There have been attempts to use ultrasonic drilling to cut a rectangular flow path through a sapphire prism to define a rectangular flow path in a sapphire detection cell. However, it is important for the flow path to have walls which are highly polished both on the inside and the outside and the rectangular flow path drilled through a sapphire prism can be polished with only one degree of motion, that is, parallel to the direction to the flow through the cell. Because the flow path can be polished with motion in only one direction, the level of polish achieved is inferior and causes the walls of the cell to scatter the light passing through the cell. In addition, the walls of the cell tends to collect particles from the flowing stream thus causing further background scatter. As a result, expensive imaging optics are utilized in the sapphire cell having the rectangular flow path drilled through the sapphire prism.

In contrast with the sapphire prism having a rectangular profile drilled therethrough, sapphire cells with round flow paths can have their inside walls polished to a satisfactory degree. This is because with a round flow path, the walls of the path can be polished with motion in two directions, axial and rotational. Even a round profile, however, cannot achieve the degree of polish that can be achieved on the quartz surfaces which are diffusion bonded together because the quartz surfaces can be polished with motion in several directions including rotary motion on the planes of the surface as well as linear motion in more than one direction on the planes of the surface. Accordingly, there is a need for a sapphire detection cell with a rectangular flow path which has the same high degree of polish that is achieved with the quartz detection cell having a rectangular flow path.

SUMMARY OF THE INVENTION

In accordance with the invention, a particle detecting instrument is provided with a sapphire cell in which the walls of the cell are made of four separate pieces which assemble into a cell with a square flow path through the middle of the cell, the flat walls of the cell including the inside walls defining the flow path in the center of the cell are each separately polished by a polishing method using motion in several directions including two linear directions on the planes of the flat faces of the sapphire pieces and a rotary motion on the planes of the flat faces. The pieces upon being assembled into the cell sandwich thin black gaskets between their opposed faces and are held tightly in their assembled configuration by means of shape memory alloy rings which shrink to engage the outside boundary of the cell to clamp the cell together. The rings engage the sapphire pieces in cylindrical end sections of the cell with the square flow path in a square section extending between the cylindrical sections.

In the preferred embodiment, the individual pieces are pie-shaped so that the cell has mitered corners at the interfaces between the pie shaped pieces.

DESCRIPTION OF THE PREFERRED EMBODIMENT

Figure 1:
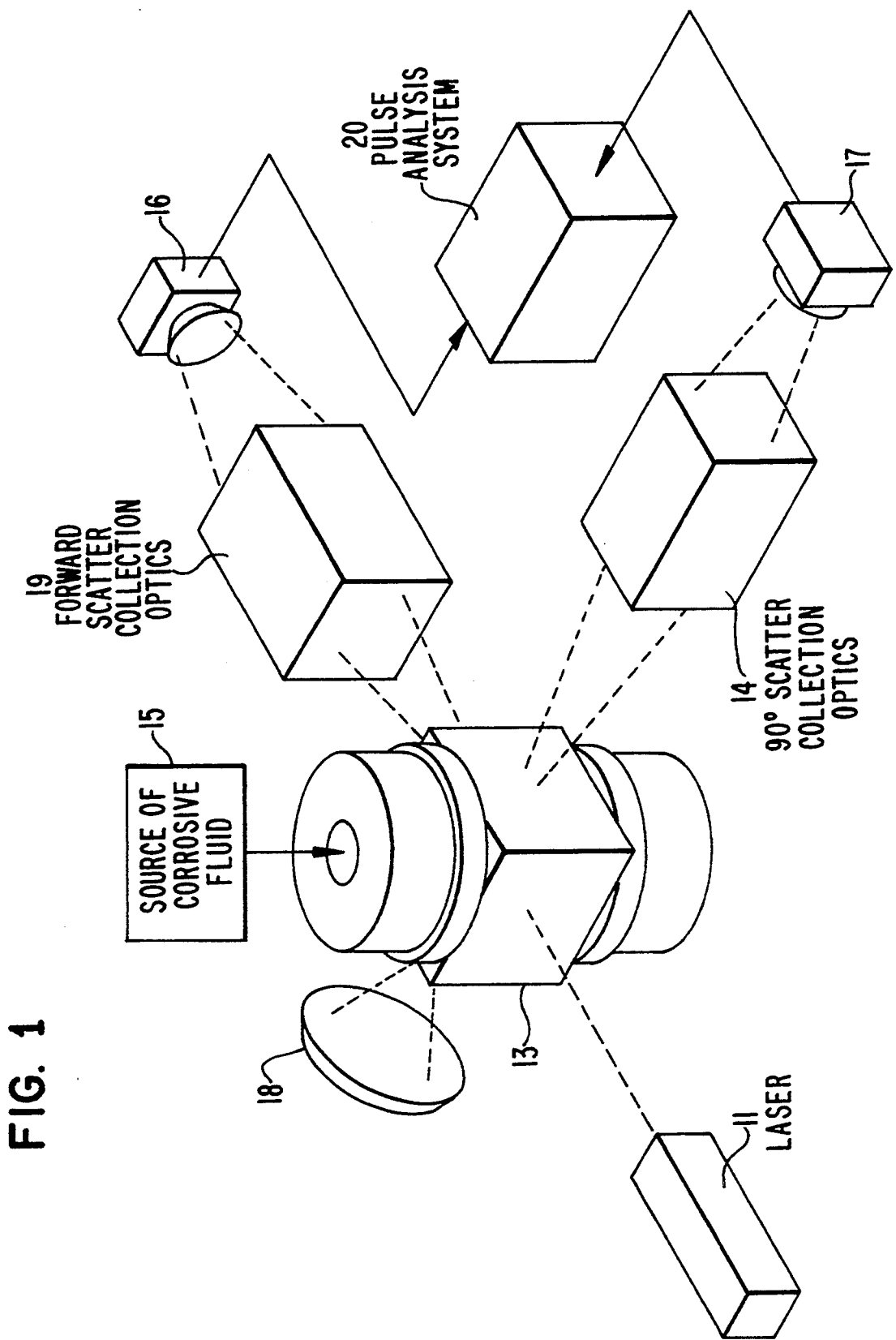
FIG. 1 schematically illustrates a partial detector making use of the improved detecting cell of the present invention.
Figure 2:
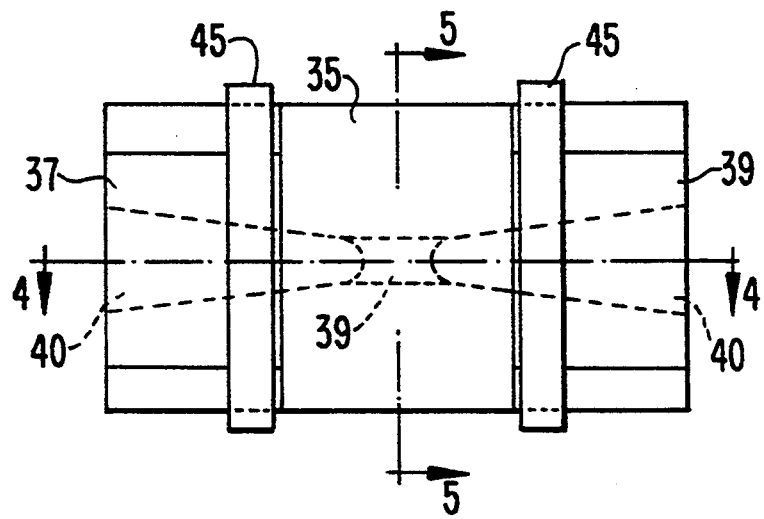
FIG. 2 is a side view in elevation of the photodetecting cell of a preferred embodiment of the invention.
Figure 3:
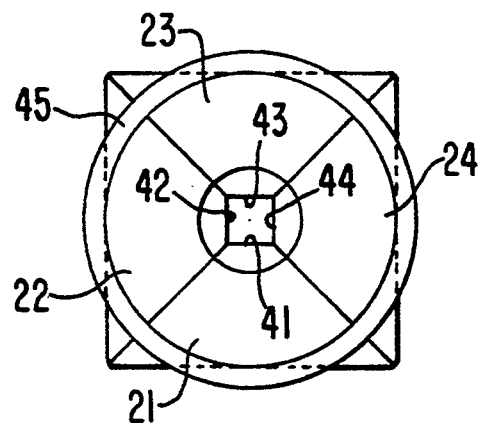
FIG. 3 is an end view of the cell shown in FIG. 2.
Figure 4:
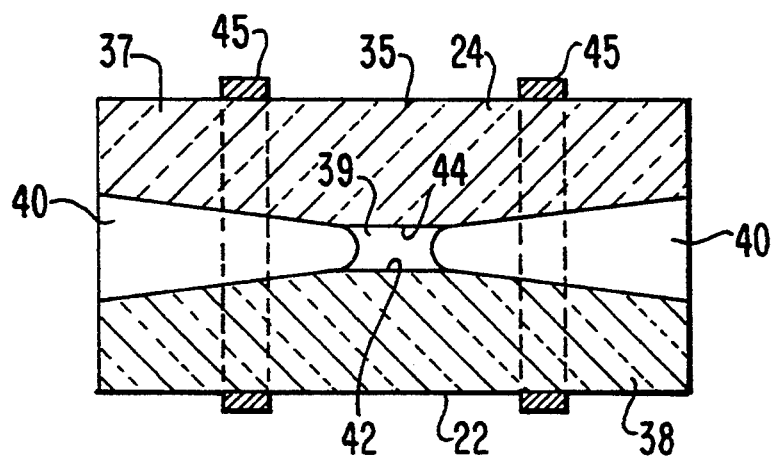
FIG. 4 is an axial sectional view through the cell taken along line 4—4 in FIG. 2.

As shown in FIG. 1, the particle detecting instrument of the present invention comprises a laser 11 for directing a beam through a particle detecting cell 13 which defines a flow path passing axially through the middle of the cell. A source 15 of corrosive liquid entraining particles to be detected causes the liquid to flow from the source 15 through the flow path defined in the cell 13. The laser beam passing through the walls of the cell 13 and through the stream of liquid in the flow path will be scattered from particles entrained in the liquid stream. Light scattered sideways from the particles in one direction is collected by 90 degree scatter collection optics 14 and detected by photodetector 17, and light scattered sidewise in the opposite direction is reflected back through the cell and through the collection optics 14 by a spherical mirror 18 to be detected by the photodetector 17. Light scattered in the forward direction from particles in the liquid stream is collected by forward scatter collection optics 19 and detected by photodetector 16. Each particle in the stream of liquid passing through the laser beam will scatter light to be detected by the 90 degree photodetector 17 and by the forward detection photodetector 16. As a result, the 90 degree photodetector 17 and the forward scatter photodetector 16 will generate a pulse in response to each particle. The output pulses from the photodetectors 17 and 16 are applied to a pulse analysis circuitry 20 which, from the amplitudes and other characteristics of the pulses, provides information as to the size of the particles in the fluid passing through the cell 13.

As shown in FIGS. 2–5, the particle detecting cell is made of four identical pie-shaped sapphire pieces 21–24, which extend throughout the length of the cell. When assembled, the pie-shaped pieces 21–24 fit together with mitered corners into the detection cell, so that the individual pieces engage each other along the diagonal interfaces. Thin black gaskets 31–34 0.0025 to 0.003 inches thick are sandwiched between an cover the opposed parallel faces of the pieces 21–24 in the diagonal interfaces. The gaskets serve to make the assembled cell liquid tight and because they absorb light, they reduce the level of background scattered light originating from the laser beam and totally internally reflected within the sapphire pieces 21–24. The gaskets are preferably made of Teflon. The assembled cell has a central section which is square in cross section with planar side walls and two end sections 37 and 38, which are cylindrical. Each pie-shaped piece in the very center of the square central section is truncated to define four planar surfaces 41–44 facing each other in the center of the cell to define a square passageway 39 in the center of the cell. This passageway connects with conical passageways 40 extending axially through the end sections 37 and 38 of the cell and partly into the square central section 35 of the cell to provide funnel-shaped passageways leading into and out of the square passageway 39 in the center of the cell.

Before assembling the four pieces 21–24 into the cell, the flat surfaces 41, 42, 43 and 44 are optically polished using a polishing method preferably moving several directions on the planes of the surfaces including a rotary motion on the planes of the surfaces and at least two linear directions in the plane of the surface. A similar optical polishing is carried out on the external flat surfaces of the square central section of the cell. After the four pieces 21–24 have been assembled into the cell as shown in FIGS. 2–5, shape memory alloy rings 45, commonly known as shrink rings, are placed over each cylindrical end section 37 and 38 of the cell and are heated to shrink the rings 45 onto the cylindrical surfaces of the end sections of the cell to hold the four pieces 21–24 and the gaskets 31–34 tightly together with enough force to prevent any leakage in the diagonal interfaces.

Because the cell walls are made out of sapphire, the walls of the cell are not subject to being corroded by a corrosive liquid flowing through the cell. Because the center of the cell through which the laser beam passes and through which light scattered from particles passing through the center of the cell is rectangular, the laser beam can be expanded to cover a much larger portion of the cell than is possible with a cell having only a passageway which is round in cross section, e.g., over 90 percent of the cell for detecting particles 0.2 microns in diameter, and over 4 percent of the cell for detecting particles 0.1 micron in diameter as compared to less than 1 percent of cells with round passageways. Also, because the cell is assembled from pieces, the cell can be polished to a much higher degree than cells having passageways which are bored through the cell and, thus, the cell does not have the disadvantage of generating a high level of background scattered light from the walls of the cell. Because all cell walls are made of sapphire, scattered light can be collected at right angles to the illuminating beam.

Figure 5:
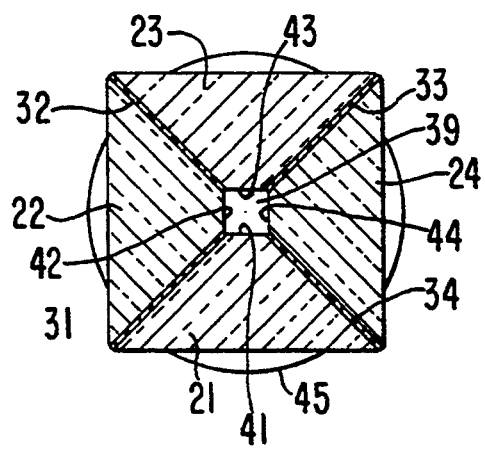
FIG. 5 is a cross sectional view taken through the center of the cell along line 5—5 of FIG. 2.
Figure 6:
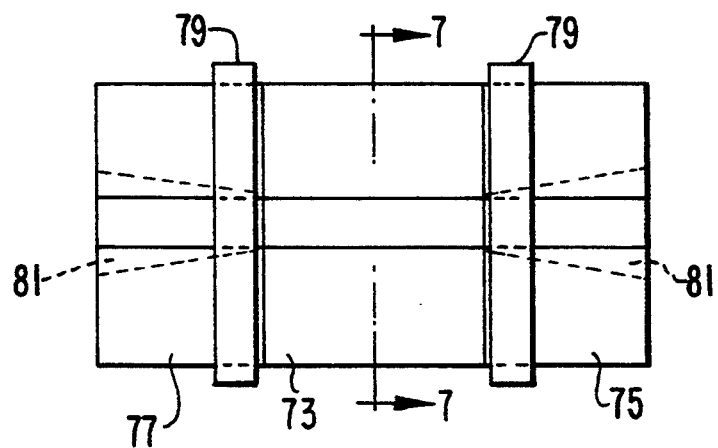
FIG. 6 is a side view in elevation of an alternative embodiment of the cell in accordance with the present invention.
Figure 7:
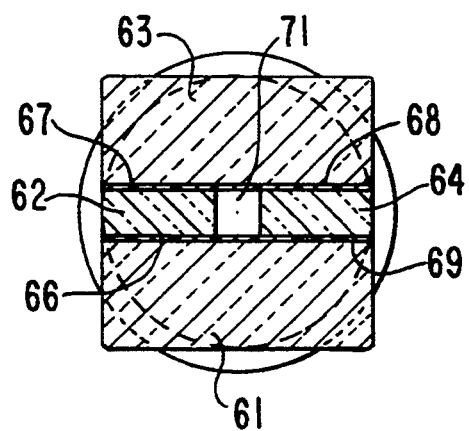
FIG. 7 is a cross sectional view of the cell of FIG. 6 taken through the center of the cell along line 7—7 of FIG. 6.

In the embodiment shown in FIGS. 6 and 7, the cell instead of being made of four pie-shaped pieces being assembled into a cell with mitered corners, the cell is made up of four pieces 61–64 with the larger pieces 61 and 63 sandwiching two smaller pieces 62 and 64 therebetween. Thin black Teflon gaskets 66–69 0.0025 to 0.003 inches thick separate and cover the opposed parallel faces of the pieces 61–64 in the interfaces where pieces connect with each other. The pieces 61 and 63 as well the pieces 62 and 64 are rectangular in cross section in the center of the cell as shown in FIG. 5 and together they define a square flow path 71 passing through the center of the cell. The pieces 62 and 63 have a dimension equal to the dimension of the square flow path 71 in the center of the cell. The cell has a central section 73 which is square in cross section with planar side walls and in the center of which the square flow path 71 is located, and two cylindrical end sections 75 and 77. The assembled pieces are held together with the gaskets 66–69 by shape memory alloy rings 79 clamping the cell around the cylindrical end sections 75 and 77. As with the cell in FIGS. 2 and 3, the flat surfaces defining a rectangular flow path 71 in the center of the cell, as well as the outside surfaces in the square central section 73, are optically polished with the polishing action in at least two dimensions in the planes of the flat surfaces as well as with rotary motion to achieve a highly polished, optically flat surface on the inner and outer walls of the cell. As with the embodiment of FIGS. 2–4, conical passageways 81 extend axially through the cylindrical end sections and connect with the square center passageway 71.

Because there are no mitered corners to orient the pieces in the cell and hold them in their oriented positions, each piece of the cell of FIGS. 6 and 7 must be carefully positioned before the shape memory alloy rings are applied to the cell to hold it together. In the preferred embodiment, outside surfaces of the pieces 62 and 64 are cylindrical in the end sections 75 and 77 to conform with the cylindrical outside surfaces of the pieces 61 and 63. Since the pieces 62 and 64 do not need to have any substantial compressive force applied to their outside surfaces by the rings 79, the outside surfaces can be flat instead of cylindrical.

The above description is of preferred embodiments of the invention and modifications may be made thereto without departing from the spirit and scope of the invention which is defined in the appended claims.

We claim:

1. A particle measuring instrument comprising a particle detecting cell defining a flow path, at least part of which is rectangular in cross section, and having sapphire walls, means to transmit a light beam through the walls of said part of said flow path, means to detect light scattered from particles passing through said light beam from said part of said flow path, said cell comprising four assembled sapphire pieces each having a flat optically polished inner surface defining one inner wall of said part of said flow path, said sapphire pieces being shaped to connect with each other in unbonded interfaces between opposed parallel faces of said sapphire pieces when assembled in said cell, and clamping means to clamp said pieces together in an assembled detecting particle cell, said clamping means pressing said parallel faces together with sufficient force to prevent leakage through said interfaces.

2. A particle measuring instrument as recited in claim 1, wherein said pieces are pie-shaped and said interfaces comprise mitered corners in said assembled particle detecting cell.

3. A particle measuring instrument as recited in claim 1, wherein said opposed faces sandwich gaskets therebetween.

4. A particle measuring instrument as recited in claim 3, wherein said gaskets, are black.

5. A particle measuring instrument comprising a particle detecting cell defining a flow path, at least part of which is rectangular in cross section, and having sapphire walls, means to transmit a light beam through the walls of said part of said flow path, means to detect light scattered from particles passing through said light beam from said part of said flow path, said cell comprising four assembled sapphire pieces each having a flat optically polished inner surface defining one inner wall of said part of said flow path, said sapphire pieces being shaped to connect with each other in interfaces between opposed parallel faces of said sapphire pieces when assembled in said cell, said clamping means comprising rings shrunk fit upon said cell.

6. A particle measuring instrument as recited in claim 5, wherein said rings are shape memory alloy rings.

7. A particle measuring instrument comprising a particle detecting cell defining a flow path, at least part of which is rectangular in cross section, and having sapphire walls, means to transmit a light beam through the walls of said part of said flow path, means to detect light scattered from particles passing through said light beam from said part of said flow path, said cell comprising four assembled sapphire pieces each having a flat optically polished inner surface defining one inner wall of said part of said flow path, said sapphire pieces being shaped to connect with each other in interfaces between opposed parallel faces of said sapphire pieces when assembled in said cell, and clamping means to clamp said pieces together in an assembled detecting particle cell, said cell comprising a central section having planar exterior walls containing said part of said flow path and cylindrical end sections having cylindrical walls surrounding said flow path, said clamping means engaging said cell on said cylindrical walls.

8. A particle measuring instrument as recited in claim 7, wherein said clamping means comprises rings shrunk fit upon said cell.

9. A particle measuring instrument as recited in claim 8, wherein said rings are shape memory alloy rings.

10. A particle measuring instrument comprising a particle detecting cell defining a flow path, at least part of which is rectangular in cross section, and having sapphire walls, means to transmit a light beam through the walls of said part of said flow path, means to detect light scattered from particles passing through said light beam from said part of said flow path, said cell comprising four assembled sapphire pieces each having a flat optically polished inner surface defining one inner wall of said part of said flow path, said sapphire pieces being shaped to connect with each other in interfaces between opposed parallel faces of said sapphire pieces when assembled in said cell, and clamping means to clamp said pieces together in an assembled detecting particle cell, said pieces being pie-shaped and said interfaces comprising mitered corners in said assembled particle detecting cell, said cell comprising a central section having planar exterior walls containing said part of said flow path and cylindrical end sections having cylindrical walls surrounding said flow path and said clamping means engaging said cell on said cylindrical walls.

11. A particle measuring instrument as recited in claim 10, wherein said clamping means comprises rings shrunk onto said cylindrical sections.

12. A particle measuring instrument as recited in claim 11, wherein said rings comprise shape memory alloy rings.

13. A particle detecting cell comprising four pieces of sapphire assembled into a cell to define a flow path at least a part of which is rectangular in cross section, said sapphire pieces having flat optically polished inner surfaces to define the walls of said part of said flow path, said sapphire pieces being shaped to connect with each other in unbonded interfaces between opposed parallel faces of said sapphire pieces in an assembled cell, and clamping means to clamp said pieces together into an assembled cell, said clamping means pressing said opposed parallel faces together with sufficient force to prevent leakage through said unbonded interfaces.

14. A particle detecting cell as recited in claim 13, wherein said pieces are pie-shaped and wherein said interfaces between said pieces comprise mitered corners in said assembled cell.

15. A particle detecting cell as recited in claim 13, wherein said opposed faces sandwich gaskets therebetween.

16. A particle detecting cell as recited in claim 15, wherein said gaskets are black.

17. A particle detecting cell comprising four pieces of sapphire assembled into a cell to define a flow path at least a part of which is rectangular in cross section, said sapphire pieces having flat optically polished inner surfaces to define the walls of said part of said flow path, said sapphire pieces being shaped to connect with each other in interfaces between opposed parallel faces of said sapphire pieces in an assembled cell, and clamping means to clamp said pieces together into an assembled cell, said clamping means comprising rings shrunk fit upon said assembled cell.

18. A particle detecting cell as recited in claim 17, wherein said rings comprise shape memory alloy rings.

19. A particle detecting cell comprising four pieces of sapphire assembled into a cell to define a flow path at least a part of which is rectangular in cross section, said sapphire pieces having flat optically polished inner surfaces to define the walls of said part of said flow path, said sapphire pieces being shaped to connect with each other in interfaces between opposed parallel faces of said sapphire pieces in an assembled cell, and clamping means to clamp said pieces together into an assembled cell, said assembled cell having cylindrical end sections with cylindrical walls surrounding said flow path and a central section having planar walls and containing said part of said flow path, said clamping means engaging said sapphire pieces on said cylindrical walls.

20. A particle detecting cell as recited in claim 19, wherein said clamping means comprises rings shrunk fit onto said cylindrical end sections.

21. A particle detecting cell as recited in claim 20, wherein said rings comprise shape memory alloy rings.

22. A particle detecting cell comprising four pieces of sapphire assembled into a cell to define a flow path at least part of which is rectangular in cross section, said sapphire pieces having flat optically polished inner surfaces to define the walls of said part of said flow path, said sapphire pieces being shaped to connect with each other in interfaces between opposed parallel faces of said sapphire pieces in an assembled cell, and clamping means to clamp said pieces together into an assembled cell, said pieces being pie-shaped and said interfaces between said pieces comprising mitered corners in said assembled cell, said assembled cell having cylindrical end sections with cylindrical walls surrounding said flow path and a central section containing said part of said flow path and having planar exterior walls, said clamping means engaging said sapphire pieces on said cylindrical walls.

23. A particle detecting cell as recited in claims 22, wherein said clamping means comprise rings shrunk fit onto said cylindrical end sections.

24. A particle detecting cell as recited in claim 23, wherein said rings comprise shape memory alloy rings.

* * * * *